Figure 1:
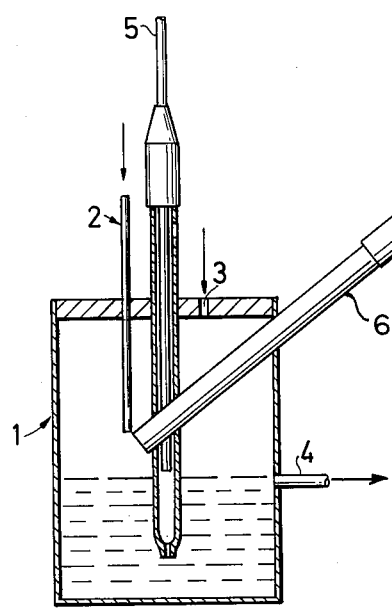

United States Patent [19]

Ruzicka et al.

[11] 4,227,973
[45] Oct. 14, 1980

[54] AUTOMATIC ANALYSIS OF ALKALI METALS HALIDES ETC. BY MEANS OF THE USE OF ION-SELECTIVE ELECTRODES

[75] Inventors: Jaromir Ruzicka, Naerum; Elo H. Hansen, Lyngby, both of Denmark

[73] Assignee: Bifok AB, Sollentuna, Sweden

[21] Appl. No.: 832,742

[22] Filed: Sep. 12, 1977

[30] Foreign Application Priority Data

Sep. 15, 1976 [SE] Sweden .............................. 7610221

[51] Int. Cl.$^2$ .............................................. G01N 27/46
[52] U.S. Cl. ................................ 204/1 T; 204/195 R; 204/195 G; 204/195 M
[58] Field of Search .................. 204/1 T, 1 H, 195 R, 204/195 G, 195 M, 1 A

[56] References Cited

U.S. PATENT DOCUMENTS

| | | | |
|---|---|---|---|
| 2,108,293 | 2/1938 | Perley | 204/195 G |
| 3,241,430 | 3/1966 | Kulick | 356/150 |
| 3,296,098 | 1/1967 | Arthur | 204/195 G |
| 3,320,148 | 5/1967 | Skeggs | 204/180 R |
| 3,427,135 | 2/1969 | Pelavin et al. | 422/64 |
| 3,556,950 | 1/1971 | Dahms | 204/195 R |
| 3,572,994 | 3/1971 | Hochstrasser | 210/321 R |
| 3,600,953 | 8/1971 | Isreeli et al. | 73/713 |
| 3,840,438 | 10/1974 | Ast et al. | 204/1 T |
| 3,853,732 | 12/1974 | Brand | 204/195 F |
| 3,997,420 | 12/1976 | Buzza | 204/195 M |
| 4,022,575 | 5/1977 | Hansen et al. | 73/425.4 R |

*Primary Examiner*—G. L. Kaplan
*Attorney, Agent, or Firm*—Finnegan, Henderson, Farabow, Garrett & Dunner

[57] ABSTRACT

A method and an apparatus for instantaneously determining ions in a carrier solution by means of leading it into a very thin continuous layer over the sensitive surface of an ion-selective electrode in a measuring cell and, from said measuring cell, on to a reservoir having a reference electrode so that the potential difference between the electrodes in the measuring cell can be continuously registered. The apparatus consists of a circuit having an inlet conduit, a pump, a sample addition apparatus, a loop, the measuring cell and a conduit via the pump to an outlet. The liquid level in the measuring cell is held constant, the ion-selective electrode being arranged above the liquid level and the reference electrode being immersed in the solution.

4 Claims, 8 Drawing Figures

AUTOMATIC ANALYSIS OF ALKALI METALS HALIDES ETC. BY MEANS OF THE USE OF ION-SELECTIVE ELECTRODES

Automatic analyzers are previously known, for example, by U.S. Pat. Nos. 3,241,430; 3,320,148; 3,427,135; 3,572,994; 3,600,953; etc. An improved continuous analyzer which operates without segmenting air bubbles in the liquid flow is described in U.S. Pat. No. 4,022,575, and the present invention is preferably intended for use in connection with said latter analyzer even if it, naturally, can be used for the older types. The construction and function of the analyzers is described in detail in the above-mentioned patent specifications and in U.S. Pat. No. 4,177,677 which, furthermore, relates especially to an improved automatic sample supply to a continuous analyzer without segmenting air bubbles, and thereby supplements the developement of this kind of analyzer from a concept having a simple flow system to systems which allow repeated addition of reagents, flow division, multiple analysis and then dialysis or ultrafiltration.

However, the measurements in all these cases are almost exclusively made by spectrophotometry. The present invention relates to the use of potentiometric detectors for the actual measuring, which, for several reasons, entails great advantages. During recent years, a large number of ion-sensitive electrodes has been developed, and beyond the well-known glass electrode for pH measurements, there are now fluoride electrodes, polymer-based potassium and calcium electrodes, the newly-developed nitrate electrode, etc.

The advantages associated with the use of electrodes is the simplicity of the experimental setup, selectivity, sensitivity, fast response and relatively simple chemistry which usually only comprises adjustment of ionic strength and pH. On the other hand, the interpretation of the readout can be difficult if the ion to be determined exists in partially complexed form in the sample solution, as the total content then will be quite different from the ionic activity sensed by the electrode. Another disadvantage of the electrodes lies in the fact that they sense the ionic activity in the immediate vicinity of the membrane, which means that each time there is a change in the composition of the solution, an equilibrium between the bulk and the diffusion layer adhering to the electrode surface has to be reestablished. Thus, even fast responding electrodes might show an erroneous readout if the stirring is not adequate, although the same stirring rate would be sufficient for spectrophotometric measurements where the bulk of the solution is being monitored continuously.

For the equilibration of an electrode, governed by the activity changes in the bulk of the solution as well as the ionic diffusion in the electrode membrane and the outer solution surrounding it, it was shown that the measured potential $E_t$ at time t reaches its equilibrium value according to the equation $$E_t - E_\infty = \frac{RT}{zF} - \ln\left[1 - (1 - \frac{a_{Mz} + (o)}{a_{Mz} + (\infty)})B\right]$$

where (o) refers to time zero and ($\infty$) to infinity where a true steady state signal is reached ($E = E_\infty$), and where B equals to exp. ($-t/\tau$) for membranes with negligible inner diffusion, while for the neutral carrier membranes $$B = \frac{1}{\sqrt{t/\tau + 1}}.$$

In both cases $\tau = k\delta^2$ where k is a lump constant involving diffusion of ions in the membrane, in the carrier electrolyte, and in the stagnant boundary layer, the latter having thickness $\delta$. Experiments with valinomycin-diphenylphthalate-PVC membranes have shown that the thickness of the surface film $\delta$ of the outer electrolyte is of vital importance, and in vigorously stirred solutions a value of $\tau = 1$ msec was observed, while in slowly mixed solutions much higher values were found. Therefore it can be concluded that in batch measurements the governing factor of the signal-in-time function is determined by the stirring rate, electrode geometry and the way in which the sample is being introduced into the measuring vessel, and not the slow response of the electrode itself.

In the continuous analyzer accordin to our U.S. Pat. No. 4,022,575, well-controlled mixing conditions are achieved so that the concentration profile formed in the continuous flow system becomes the governing factor of the response curve. Consequently, the concept of "steady state" in electrode measurements is avoided. In order to minimize $\delta$ and obtain optimum washout yet to avoid any pressure changes in the ion-selective membrane, the usual tubular arrangement is, according to the present invention, replaced by a new type of a flow cell in which only a thin stream of the carrier electrolyte tangentially is pumped across the electrode surface. The examples clearly show the surprising effect of the invention in tests carried out with a potassium valinomycin based electrode with PVC membrane, a sodium neutral carrier PVC electrode and a newly developed nitrate electrode used as sensors in single and multiple potentiometric analyses.

Figure 2:
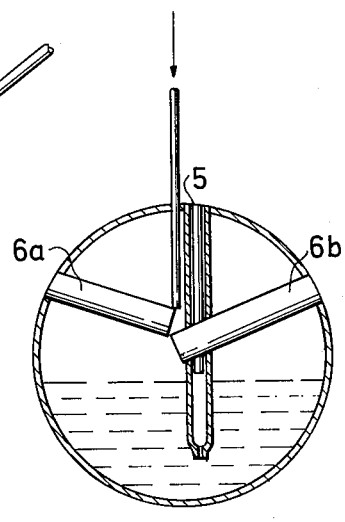
Figure 3:
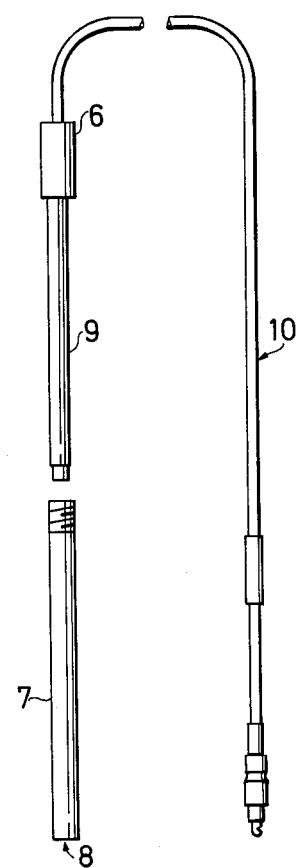
Figure 4:
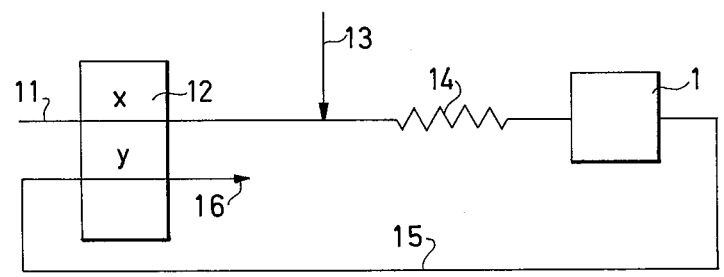
Figure 5:
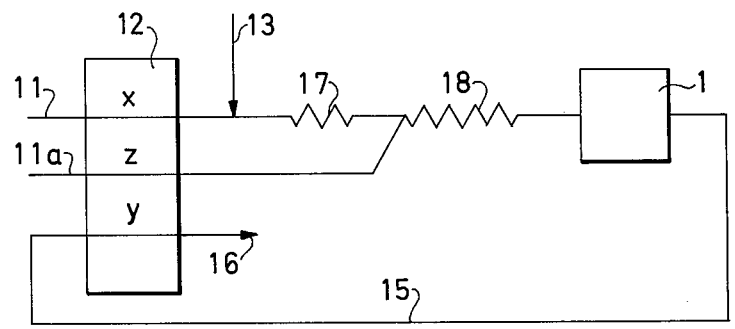
Figure 6:
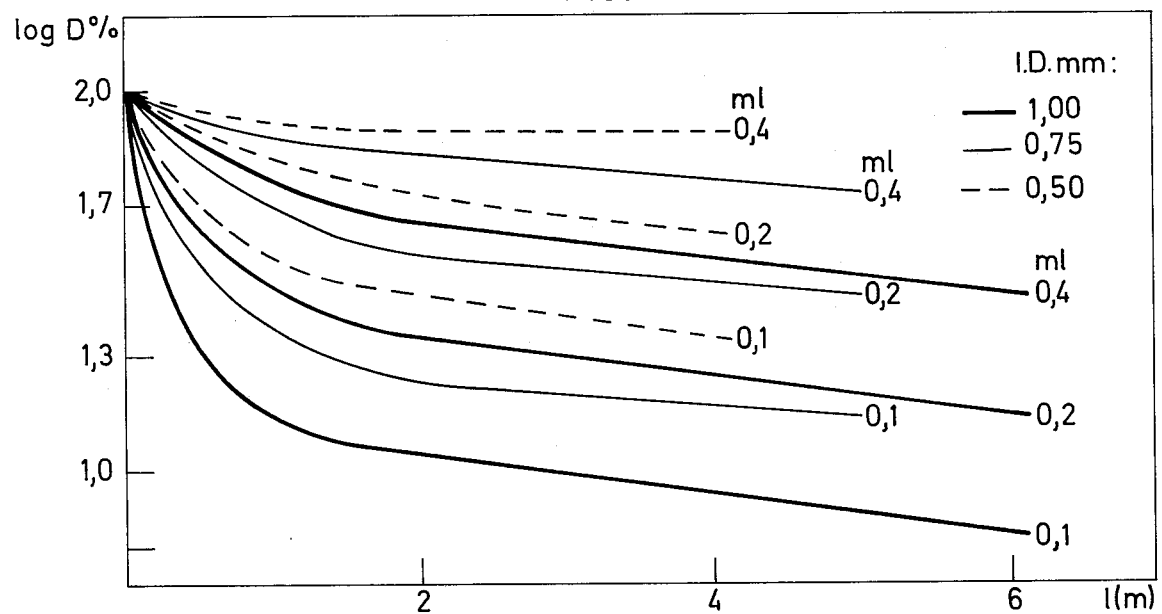
Figure 7:
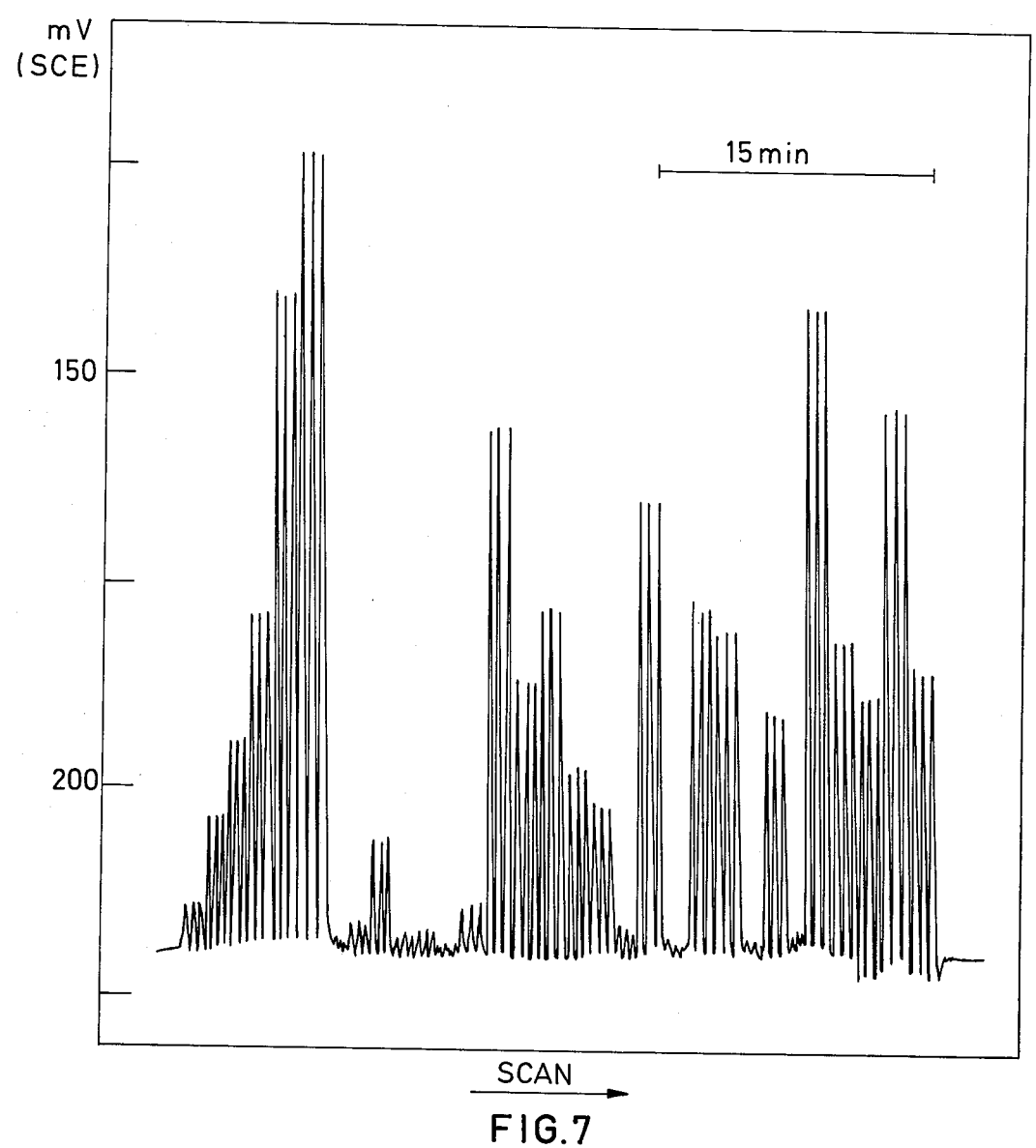
Figure 8:
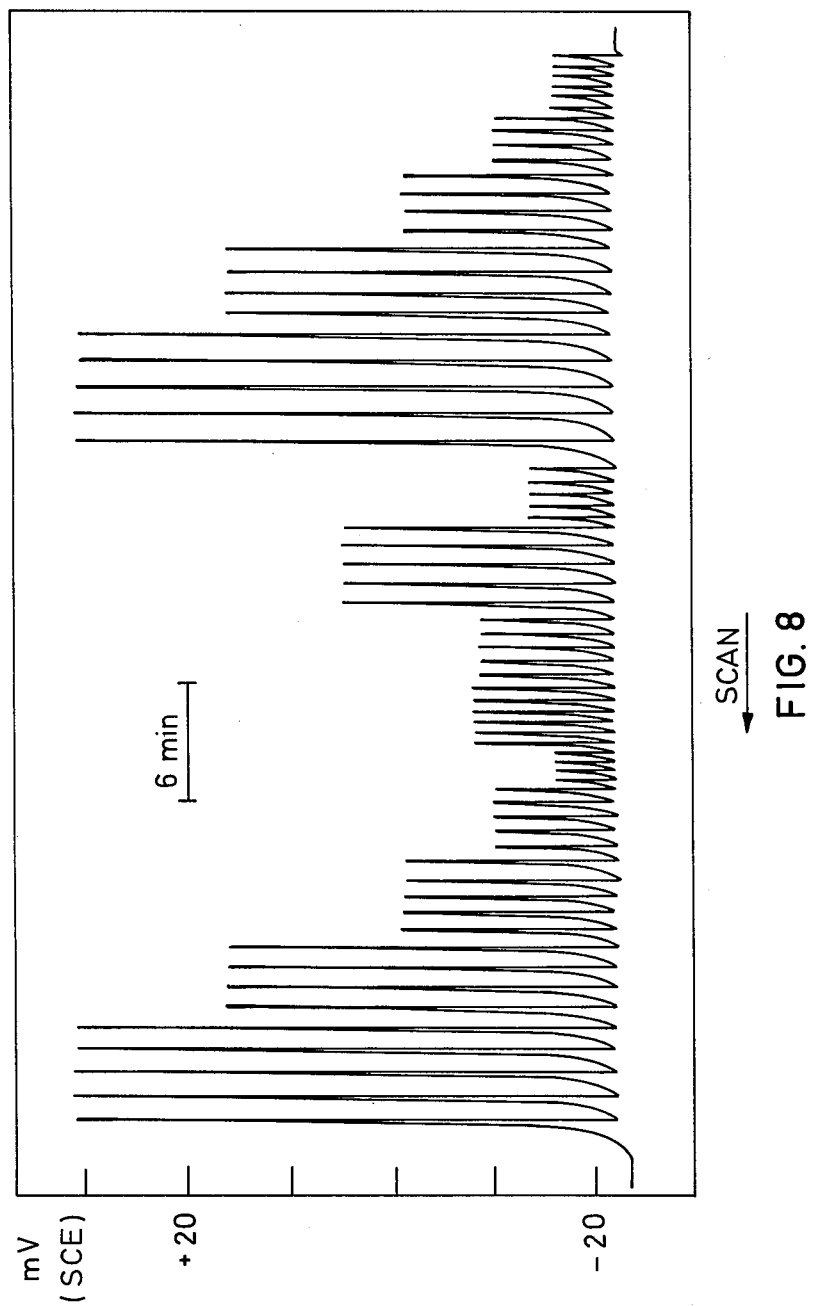

The invention will be described in more detail in connection with the accompanying drawings, in which FIG. 1 is a flow cell according to the invention having a membrane electrode, FIG. 2 is a flow cell having two membrane electrodes, FIG. 3 is a blow-up of the used electrode, FIG. 4 is a straight appratus setup, FIG. 5 is a branched setup, FIG. 6 is the dilution factor as a function of the tube length, sample volume and tube diameter, FIG. 7 is measurements of the nitrogen in waste water samples and earth extract, and FIG. 8 is the measurement of potassium in earth extract at a speed of 80-90 samples per hour.

The flow cell 1 is made of Perspex ® and provided with an inlet tube 2 for the carrier flow, an inlet hole 3 for air, an outlet 4 for the examined sample, a reference electrode 5 and an ion-selective electrode 6. The constant liquid level in the flow cell is maintained by means of differential pumping, pump-in always being held 30-50% lower than pumping-out.

The reagents for the measurements have been of A.R. quality and redistilled water has been used throughout. Serum samples consist of freeze-dried standard materials, Monitrol I and II, prepared according to the manufacturer's instructions.

A silver-silver chloride electrode or a saturated calomel electrode is used as a reference electrode. The ion-selective electrode 6 consists of a rigid PVC tube 7 having an end opening of 7 mm², upon which a PVC membrane 8 is glued by means of a 4% PVC solution in tetrahydrofuran. The electrode is then filled with the inner electrolyte solution and is stored in conditioning conditions during the night and between measurements. The tube 7 has an outer diamter of 9.5 mm and a length of 103 mm. Radiometer's electrode construction F2002, (Ag/AgCl) has been used as reference electrode for all measurements. The electrode is connected to a pH-meter by means of a cable 10. The pH-meter is, in turn, connected to a recorder.

A large number of experiments have been carried out to determine the effect of the carrier stream on the membrane, the electrode angle and the immersion depth of the electrode, the electrode active area, the flow rate and the cell holdup on signal stability, speed of response and carryover. In the final arrangement, the dead volume of the cell was 5 to 10 μl, being constituted by only that portion of the electrolyte layer which covered the membrane opening of the electrode. This electrolyte layer is approximately 1 mm thick. Thus, with a flow of only 2 ml/min., the layer of electrolyte is renewed approximately five times per second. The tangential flow was found to give the most effective wash while the smallest possible immersion of the electrode gives optimum washout which is critical in serum analysis, when more viscous materials tend to increase the carryover between subsequent measurements. The cascade flow arrangement shown in FIG. 2, however simple, gave surprisingly reproducible results and noiseless signals. The two ion-selective electrodes 6a and 6b just barely touched each other to achieve a good washout, yet to ensure sufficient electrical contact between both electrodes and the reference electrode.

The potassium electrode used was based on valinomycin, was furnished with a PVC membrane containing dioctyladipate as plasticizer. The inner reference solution was $1 \cdot 10^{-2}$ M KCl, the conditioning solution was $1 \cdot 10^{-1}$ M KCl and the conditioned electrode had a slope of 59 mV/decade.

The sodium electrode was based on a neutral carrier dissolved in dibutylsebacate and incorporated into PVC. The inner reference solution was $1 \cdot 10^{-2}$ M NaCl, the conditioning solution was $1 \cdot 10^{-1}$ M NaCl, and the conditioned electrode had a slope of 60 mV/decade.

The nitrate electrode was based on tetraoctylammonium bromide combined with dibutylphthalate as plasticizer in PVC, with the inner reference solution of $1 \cdot 10^{-2}$ M $NaNO_3 + 1 \cdot 10^{-2}$ M NaCl, the conditioning solution $1 \cdot 10^{-1}$ M $KNO_3$, the slope being 59 mV/decade. The apparatus construction is shown schematically in FIGS. 4 and 5. The carrier solution passes through the tube 11 through the pump 12 to sample addition 13 through the loop 14 to the measuring cell 1. From the measuring cell 1, the tube 15 leads to the pump 12 which pumps the solution out through the outlet 16.

In FIG. 5, the loop 14 is divided up into two sections 17 and 18, and the carrier solution is pumped through a branched conduit 11a in between the two loop sections. The pump-in speed x and z is disclosed in the tests, and the pump-out speed y was then chosen 30–50% higher than x or x+z in order to maintain a constant liquid level in the potentiometric flow cell 1 with the reference electrode and the ion-selective electrode or electrodes. All of the tubes had an inner diameter of 1.00 mm when nothing else is disclosed, but in such cases, tubes having another inner diameter only constitute that part of the conduit which lies between the sample supplying position 13 and the flow cell 1.

When the added sample passes through the apparatus, it becomes gradually mixed with the carrier flow and the thus created concentration profile forms a peak with a rising and falling edge which are reversals of each other and intersect at a point the distance of which, above the baseline, constitutes the peak height. The rising edge is characterized by the equation:

$$c_t = c_o (1 - e^{-Rt/V})$$

where R is the volume of the carrier solution mixed with the sample plug of volume V per second and t is the time during which the sample plug moves from the point of sample supply to the point of measurement. The equation applies, however, only for short lines and/or low R values. Thus, providing that $\tau$ is smaller than R/V, the electrode response will be much faster than the mixing process within the line and therefore the latter process will control the response time.

As the sample zone moves along the line, the sample material becomes progressively more diluted and this process can be described by a dilution factor D. The dilution as a function of tube length, sample volume and tube I.D. is shown in FIG. 6, from which the conclusion can be drawn that a wide choice of D values, 10% to 90%, is available in an analyzer system. Thus, a short line will give a high sampling ratio and low dilution, high D factor, while a long line will yield the opposite result. If a chemical reaction, e.g. masking or buffering, prior to the electrode measurement is required, a very short line might not suffice and poorly reproducible results will be obtained. Therefore, either a long line, which could give a lower sampling rate, or a confluence system according to FIG. 5 which gives more effective and faster mixing is used.

The effect of the pumping speed on the dilution factor has also been examined and, contrary to what could be expected, the dilution decreases with decreased pumping speed, a fact which contradicts the hypotheses that turbulent flow, as opposed to laminar flow, is essential in order to prevent peak dissipation and broadening of the sample zone.

The electrodes have been calibrated in a flow of carrier solution under exactly the same conditions used in the different examples. The examples below disclose a couple of the analyses in which the present invention can be advantageously used.

EXAMPLE 1

Determination of Potassium in Soil Extracts.

Determination of potassium in soil extracts and blood is generally performed by flame photometry, but the use of electrodes for this purpose has the advantage of simplifying the instrumentation and decreasing the cost of analysis. At the same time, the nature of these two types of sample material are so essentially different that it offers an interesting and difficult testing ground for the new technique.

The soil samples were extracted by means of 1 M $NH_4Ac$, 1.0 M and 0.2 M NaAc and 0.5 M $NaHCO_3$ and then analysed according to the invention, FIG. 8, and flame photometry. The analysis speed was 80–90 samples per hour and a potassium electrode was used with a straight apparatus setup according to FIG. 4 in which the loop 14 was 0.65 m.×4.0 ml/min., and the carrier flow consisted of 1.0 M NaAc. Five standards, $1\times10^{-4}$ M, $2\times10^{-4}$ M, $4\times10^{-4}$ M, $1\times10^{-3}$ M and $2\times10^{-3}$ M KCl in 1.0 M NaAc followed by four earth extracts are shown from right to left in FIG. 8. Thereafter, the same series of five potassium standars follows again, and all the samples were injected in an amount of 0.2 ml with four or five repetitions. There were two reasons for using several extracting solutions for soil analysis. The most widely used extractant, 1 M ammonium acetate, is not suitable in connection with a potassium valinomycine-based electrode as a high amount of ammonium interferes in the determination of low potassium contents. As soil extraction is an ion exchange process, the use of sodium acetate of the same concentration can lead to quite similar results, as indicated in table I. Furthermore, use of more diluted sodium acetate (0.2 M) results in lower relative potassium values, but is economically advantageous, which is important in many cases.

The analysis results are arranged in table I which shows that good correlation was obtained between the two sodium acetate extractions, even if soil samples having low clay content generally provided low R values.

TABLE I

| Soil No. | 1 M NH4Ac Fl.Ph. | 1 M NaAc Fl.Ph. | 1 M NaAc Pot. | 0.5 M NaHCO3 Fl.Ph. | 0.5 M NaHCO3 Pot. | 0.2 M NaAc Pot. | $R^{(x)}$ |
|---|---|---|---|---|---|---|---|
| 1 | 18.1 | 18.0 | 18.1 | 15.7 | 16.0 | 13.0 | 1.39 |
| 2 | 20.6 | 20.5 | 21.6 | 17.8 | 18.4 | 14.2 | 1.52 |
| 35 | 17.5 | 16.8 | 18.5 | 17.6 | 17.6 | 12.1 | 1.53 |
| 22 | 17.2 | 16.7 | 17.9 | 17.3 | 16.7 | 14.9 | 1.20 |
| 39 | 15.7 | 16.4 | 16.2 | 16.1 | 14.9 | 11.9 | 1.36 |
| 19 | 13.6 | 14.1 | 13.9 | 12.7 | 13.6 | 10.5 | 1.32 |
| 26 | 10.6 | 10.7 | 11.1 | 10.7 | 11.5 | 9.5 | 1.17 |
| 6 | 8.6 | 8.6 | 9.7 | 7.6 | 7.5 | 6.1 | 1.59 |
| 32 | 4.3 | 5.2 | 6.2 | 4.1 | 4.3 | 4.1 | 1.51 |
| 18 | 4.5 | 6.6 | 6.8 | 5.2 | 5.0 | 5.5 | 1.24 |

$$^{(x)}R = \frac{POT(1\ M\ NaAc)}{POT(0.2\ M\ NaAc)}$$

EXAMPLE 2

Determination of Potassium in Blood Serum.

Although flame photometry is well entrenched as a method of determination of potassium and sodium in blood, there is a tendency to replace it by potentiometric procedures which are better suited for automatic analysis. In order to investigate formation as to the correlation between these two types of measurement, a series of blood samples, i.e. aqueous standards, serum pool and serum standard reference materials, (Monitrol I and II) were simultaneously analyzed by flame photometry and continuous automatic analysis with ion-selective electrodes. As carrier flow, a 0.14 M NaCl solution was used, pumped at a rate of 4 ml/min in the straight apparatus setup in FIG. 4. The results, summerized in Table II, confirm that there is no systematic difference between these two types of measurements.

TABLE II

| Serum sample | Content in mmol/l | |
|---|---|---|
| | Flame Photometry | Continuous Potentiometric Analysis |
| 1 | 4.0 | 3.97 |
| 2 | 5.0 | 5.03 |
| 3 | 4.8 | 4.76 |
| 4 | 4.9 | 4.88 |

TABLE II-continued

| Serum sample | Content in mmol/l | |
|---|---|---|
| | Flame Photometry | Continuous Potentiometric Analysis |
| Monitrol I | 4.4 | 4.39 |
| Monitrol II | 5.9 | 5.85 |

EXAMPLE 3

Determination of Nitrate in Waste Water Samples and Soil Extracts.

For the nitrate determinations, a branched apparatus setup according to FIG. 5 was used, in which the first mixing loop 17 was 0.40 m while the 18 mixing loop was 1.4 m, both having an inner diameter of 1.00 mm. The pumping rates of lines x and z were both 3.5 ml/min, whereas that of line y was 9 ml/min. This arrangement was used in order to secure a thorough mixing of the samples with the phosphate buffer carrier solution and hence a stabilization of pH. A series of waste water samples and soil extracts were analyzed, of which some are shown in FIG. 7 along with a set of calibration solutions. As observed from the figure, excellent reproducibility was obtained, except in those instances where the samples due to large additions of preservatives (sulphuric acid) initially exhibited excessively low pH values (see peaks at far right of figure). Furthermore, good agreement was found between the values found by the method according to the invention and those which were obtained by other procedures, cf. Table III.

TABLE III

| Sample | Nitrate content (ppm-$NO_3^-$) | | |
|---|---|---|---|
| | Continuous pot. analysis | Auto Analyzer[a] | Electrode[b] |
| Waste-water | | | |
| 1 | 4.3 | 4.2 | — |
| 2 | 6.6 | 7.5 | — |
| 3 | 34.5 | 34.6 | — |
| 4 | 39.5 | 39.1 | — |
| 5 | 45.6 | 46.8 | — |
| 6 | 76.5 | 78.5 | — |
| Soil extract | | | |
| 1 | 6 | — | 6 |
| 2 | 9 | — | 9 |
| 3 | 12 | — | 12 |
| 4 | 75 | — | 78 |

[a]By the brucine method (±1 ppm).
[b]Samples supplied and analyzed by the State Laboratory for Soil and Crop Research; Orion nitrate electrode (92.07), calibrated every 15 min[16].

The slow, non-random change with time of a potentiometric cell, through which an electrolyte of constant composition is being pumped, is a drift which, apart from the change in temperature, is due to the change of the reference potential(s) as well as of the electrode response. The reasons for drift can be as many as are the members of the electromechanical chain: inner reference electrode, membrane and its assymetry potential, junction potential and outer reference electrode. Introduction of serum samples into an electrode is often quoted as a source of drift, or an abrupt potential change of junction and membrane potentials. The changes of temperature also affect each of these members in individual ways and the picture is even more complicated by temperature hysteresis which is well-known to be serious, especially on a saturated calomel electrode.

Thus it might immediately appear improbable that a high precision and reproducibility of measurements could have been obtained in a flow injection system which was not thermostated, and that no apparent problems were encountered when serum samples were analyzed. The reason is that by continuous automatic analysis a large number of samples is being analyzed in a short span of time and therefore all samples may readily be bracketed by sets of standards. Thus, even if the ambient temperature should change as much as 5° during a working day, corresponding to 1 mV in terms of the factor 2.3 RT/F, no problems are encountered. Although a more pronounced temperature influence might be observed if the measured activities are further removed from the isopotential point, drifts of even several millivolts per hour can nevertheless easily be corrected for by standardization. Fortunately, changes in laboratory temperatures are usually smaller and rather monotonous.

No abrupt changes of the junction potential in the presence of serum were observed, probably due to the fact that the tip of the reference electrode is located in a large reservoir, in which the serum is much diluted by the carrier electrolyte. It was, however, found most important to maintain a proper electrode configuration so that also the more viscous serum samples were effectively washed away from the membrane surface.

No electrical disturbances, as often encountered in tubular flow cells, were experienced except when the active area of the ion selective electrode was made smaller than 1 $mm^2$—which introduced a large impedance into the electrode chain. Then characteristic oscillations were observed and their magnitude was dependent on the type of pump used. Typically, pumps constructed of a combination of non-conductable and conductable moving parts were more noisy, while all-plastic or all-metal constructions gave a noiseless signal due to absence of static electricity.

Owing to high selectivity and excellent durability of the ion-selective electrodes, it was possible to develop simple, fast and reliable methods for potassium and nitrate determinations. The valinomycine potassium ion-selective electrode was furnished with the same membrane, used continuously for five months during which more than 60,000 measurements were made on samples of different origin and composition. The nitrate electrode has up to now been used for about 5,000 measurements. As a result of the automated operation a standard deviation of only 0.2 mV (corresponding to 0.8% for a monovalent ion) was typical in both measurements, when executed at a rate of 125 s/h or less. The simultaneous measurement of two ions on one stream was developed and proved to give exactly the same results as separate duplicate measurements on identical samples.

In similar manners analysis methods for fluoride and other halides, sulphide, calcium, and water hardness are also being worked out. Using proper electrodes either direct measurements as described above or techniques based on standard addition or substraction could be applied.

Also a new function of the flow injection technique using a straight apparatus setup and a high D factor can be used. Instead of allowing the sample zone to equilibrate with the carrier stream, a non-diluted sample zone can be transported to the electrode. Thus, original activities such as pH or pCa can be measured using the flow injection system merely as a means of precise timing and transport. The advantage of such an arrangement would be higher sampling rates and better reproducibility of measurement than that obtained by manual batch techniques.

What we claim is:

1. A method for determining ions in a continuously flowing liquid stream consisting essentially of a liquid sample solution in a liquid carrier comprising providing a measuring cell and an ion-selective electrode, said ion-selective electrode having a sensitive surface located in the measuring cell, freely and continuously flowing the liquid stream downwardly over the sensitive surface of the ion-selective electrode in a form of a thin, continuous sheet wherein one side of the liquid sheet is in contact with the sensitive surface of the ion-selective electrode as the sheet flows across the sensitive surface while the other side of the liquid sheet is exposed to the atmosphere of the measuring cell, the pressure of which is the same as the atmospheric pressure outside the cell, immediately thereafter permitting the liquid stream to flow as the same continuous sheet without interruption into a reservoir in the measuring cell consisting essentially of the liquid carrier and in which a reference electrode is placed, said ion-selective electrode being located above the liquid level in the reservoir, so that the potential difference between the electrodes in the measuring cell can be continuously determined.

2. The metod of claim 1 in which the ion-selective electrode and the reference electrode are arranged and the reference electrode has an outer surface such that the liquid stream flows downwardly along the sensitive surface of the ion-selective electrode and continuously down the reference electrode surface into the reservoir.

3. The method of claim 1 in which the sensitive surface of the ion-selective electrode is inclined to the vertical and the stream flows tangentially across said sensitive surface.

4. The method of claim 1 in which two ion-selective electrodes each having a sensitive surface inclined at an angle to the vertical are provided, the stream containing the sample solution flowing successively over the sensitive surfaces of the two ion-selective electrodes in the form of a thin, continuous sheet of liquid before the sheet flows into the reservoir.

* * * * *